(12) United States Patent
Scott

(10) Patent No.: US 11,344,450 B2
(45) Date of Patent: May 31, 2022

(54) SYSTEM AND METHOD FOR LASER CORNEAL INCISIONS FOR KERATOPLASTY PROCEDURES

(71) Applicant: AMO Development, LLC, Santa Ana, CA (US)

(72) Inventor: David D. Scott, Oakland, CA (US)

(73) Assignee: AMO Development, LLC, Santa Ana, CA (US)

( * ) Notice: Subject to any disclaimer, the term of this patent is extended or adjusted under 35 U.S.C. 154(b) by 487 days.

(21) Appl. No.: 16/138,912

(22) Filed: Sep. 21, 2018

(65) Prior Publication Data
US 2019/0021908 A1 Jan. 24, 2019

Related U.S. Application Data

(62) Division of application No. 14/611,859, filed on Feb. 2, 2015, now Pat. No. 10,080,684.

(60) Provisional application No. 61/935,471, filed on Feb. 4, 2014.

(51) Int. Cl.
A61F 9/00 (2006.01)
A61F 9/008 (2006.01)
A61B 3/107 (2006.01)
A61F 9/013 (2006.01)

(52) U.S. Cl.
CPC .......... A61F 9/00836 (2013.01); A61B 3/107 (2013.01); A61F 9/00802 (2013.01); A61F 9/00827 (2013.01); A61F 9/00831 (2013.01); A61F 9/013 (2013.01); A61F 2009/0087 (2013.01); A61F 2009/00846 (2013.01);
(Continued)

(58) Field of Classification Search
CPC .......... A61B 3/107; A61F 2009/00846; A61F 2009/00853; A61F 2009/0087; A61F 2009/00872; A61F 2009/00897; A61F 9/00802; A61F 9/00827; A61F 9/00831; A61F 9/00836; A61F 9/013
See application file for complete search history.

(56) References Cited

U.S. PATENT DOCUMENTS

| 5,459,570 A | 10/1995 | Swanson et al. |
| 5,720,894 A | 2/1998 | Neev et al. |
| 5,748,358 A | 5/1998 | Sugamata et al. |

(Continued)

FOREIGN PATENT DOCUMENTS

| EP | 0697611 A2 | 2/1996 |
| JP | 2006095318 A | 4/2006 |

(Continued)

OTHER PUBLICATIONS

International Search Report and Written Opinion for Application No. PCT/US2015/014112, dated Apr. 17, 2015, 10 pages.

Primary Examiner — Amanda K Hulbert
(74) Attorney, Agent, or Firm — Johnson & Johnson Surgical Vision, Inc.

(57) ABSTRACT

A first image of the eye is generated when the cornea of the eye is exposed to a gas. The cornea is covered with an optic of a patient interface. A second image of the eye with the patient interface over the cornea is generated. In this second image, the patient interface distorts the second image of the eye. One or more of a position or an orientation of the eye is determined in response to the first image and the second image when the patient interface has been placed over the cornea.

11 Claims, 11 Drawing Sheets

(52) U.S. Cl.
CPC ............. *A61F 2009/00853* (2013.01); *A61F 2009/00872* (2013.01); *A61F 2009/00897* (2013.01)

(56) References Cited

U.S. PATENT DOCUMENTS

| | | |
|---|---|---|
| 5,748,898 A | 5/1998 | Ueda |
| 5,957,915 A | 9/1999 | Trost |
| 5,984,916 A * | 11/1999 | Lai .................... B23K 26/0624 606/10 |
| 6,019,472 A | 2/2000 | Koester et al. |
| 6,053,613 A | 4/2000 | Wei et al. |
| 6,111,645 A | 8/2000 | Tearney et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2011/0319873 A1 | 12/2011 | Raksi et al. |
| 2011/0319875 A1 | 12/2011 | Loesel et al. |
| 2012/0203215 A1* | 8/2012 | Riedel .................... A61F 9/008 606/5 |
| 2013/0085370 A1 | 4/2013 | Friedman et al. |

FOREIGN PATENT DOCUMENTS

| | | |
|---|---|---|
| WO | 2008001284 A2 | 1/2008 |
| WO | 2008001284 A3 | 5/2008 |
| WO | 2014172621 A2 | 10/2014 |

* cited by examiner

SYSTEM AND METHOD FOR LASER CORNEAL INCISIONS FOR KERATOPLASTY PROCEDURES

CROSS-REFERENCE

This application is a divisional of and claims priority to U.S. patent application Ser. No. 14/611,859, filed Feb. 2, 2015, which claims priority to U.S. provisional No. 61/935,471 filed on Feb. 4, 2014, for which the subject matter of this disclosure is related to the following patent applications: U.S. application Ser. No. 12/048,182, filed 3 Mar. 2008, entitled "METHOD AND APPARATUS FOR CREATING INCISIONS TO IMPROVE INTRAOCULAR LENS PLACEMENT," U.S. application Ser. No. 12/048,186, filed 13 Mar. 2008, entitled "METHOD AND APPARATUS FOR CREATING OCULAR SURGICAL AND RELAXING INCISIONS," and U.S. App. Ser. No. 61/722,064, filed 2 Nov. 2012, entitled "LASER EYE SURGERY SYSTEM CALIBRATION," the entire disclosures of which are incorporated by reference and suitable for combination in accordance with embodiments disclosed herein.

BACKGROUND

This disclosure relates generally to photodisruption induced by a pulsed laser beam and to the location of the photodisruption for treating a material, such as eye tissue. Although specific reference is made to cutting tissue for surgery such as eye surgery, the embodiments described herein can be used in many ways and with many materials to treat one or more materials, including cutting optically transparent materials.

Materials can be cut mechanically with chisels, knives, scalpels, as well as other manual surgical tools such as microkeratomes. In at least some instances, however, prior cutting methods and apparatuses can be less than desirable and provide less than ideal results. Further, at least some prior methods and apparatus for cutting tissue may yield a rougher surface than would be ideal. Materials, including tissue, can be also cut with laser beams. A surgical laser beam is preferred over manual tools like microkeratomes as it can be focused accurately on extremely small amounts of tissue, thereby enhancing precision and reliability.

Surgical lasers have been used in ophthalmology for a while now, and are used to cut eye tissue such as the cornea, the capsular bag, and the crystalline lens of the eye. For example, in the commonly-known LASIK (laser-assisted in situ keratomileusis) procedure, an ultra-short pulsed laser is used to cut a corneal flap to expose the corneal stroma for photoablation with an excimer laser so as to correct a refractive condition, such as myopia, hyperopia, or astigmatism. Ultra-short pulsed lasers emit radiation with pulse durations as short as 10 femtoseconds and as long as 3 nanoseconds, and a wavelength between 300 nm and 3000 nm. Excimer lasers produce radiation in the ultraviolet range. Besides cutting corneal flaps, ultra-short pulsed lasers are used in cataract surgery.

During laser cataract surgery, ultra-short pulsed lasers are used for cutting eye tissue such as the cornea and the capsular bag to gain access to the cataractous lens. The laser is also used to cut the cataractous lens so as to soften and/or fragment the cataract before removal. Indeed, conventional ultra-short pulse laser systems have been used to treat many patients. In some instances, however, these systems provide less than ideal results. For example, sometimes, when a corneal refractive treatment is combined with a lens treatment, such as the removal of the lens cortex and nucleus from the eye, the alignment of the eye with the laser surgery system can be less than ideal, Ultra-short pulsed lasers are also used for corneal resection to prepare tissue for grafting. Prior methods and apparatuses for resecting corneal tissue for grafting purposes can also be less than ideal, meaning that fewer patients may receive the benefits of successful grafting procedures. Hence, it would be helpful to provide improved methods for resecting and grafting eye tissue to treat various eye diseases.

Many patients may have less than ideal optics of the eye. Some patients may have one or more refractive errors of the eye, such as myopia or hyperopia that can be corrected with spectacles, contact lenses, or the LASIK procedure. Patients may also have an irregularity of the cornea such as irregular astigmatism or corneal scarring. In at least some instances, these irregularities may not be easily corrected using prior surgical approaches. Among others, prior approaches to treating diseased cornea have included keratoplasty, such as penetrating keratoplasty (hereinafter "PK"). PK can sometimes result in less than ideal patient outcomes wherein the patient has less than ideal visual acuity following the procedure.

With some disease conditions, it can be helpful to replace a portion of the cornea instead of surgically penetrating it as is done in PK. For example, replacing a portion of the cornea may be helpful where the irregularity of the eye is related to a disease or a condition, including for instance, where low endothelial cell counts cause less than ideal optics of the cornea.

But, sometimes, prior methods and apparatuses to replace a diseased endothelium layer of the cornea can be less than ideal. One such approach, Descemet's membrane endothelial keratoplasty ("DMEK"), removes the endothelium and the underlying Descemet's membrane and replaces the diseased tissues with graft tissue from a donor. In other words, the endothelial layer and the Descemet's membrane is removed from the diseased eye and replaced with a healthy Descemet's membrane and endothelial cells from a donor eye. Unfortunately, the DMEK procedure can provide less than ideal outcomes in that some patients may not fully recover vision. DMEK can also be time-consuming and more complex than desired. Recently, another method that automates at least a portion of the DMEK procedure, referred to as Descemet's membrane automated endothelial keratoplasty ("DMAEK") has been used. Although corneal surgeons may find DMAEK potentially less complicated to perform, the results of DMAEK can be less than ideal as following the procedure, some patients' vision may not be fully correctable to twenty/twenty (metric six/six), or even twenty/forty (metric six/twelve).

Hence, it would be desirable to provide improved methods and apparatuses that overcome at least some of the limitations and disadvantages of prior systems and methods.

SUMMARY

Accordingly, embodiments of this invention provide improved treatment of materials such as corneal tissue that obviate one or more problems due to limitations and disadvantages of the related art. Ideally, these improved systems and methods will provide improved treatment of visual disorders and provide improved tissue-grafting and keratoplasty results. To achieve these objectives and other advantages, many embodiments disclose improved methods and apparatus for performing laser eye surgery, wherein a corneal measurement system can provide image-guided treatment of the eye. Although specific reference is made to keratoplasty and ophthalmic procedures, the embodiments described herein can be used in a number of applications for improved tissue incisions with decreased irregularity of the incised tissue surface, as well as for more accurate tissue cutting with improved healing. Among other things, these additional applications include tissue grafting of collagenous structures in cardiology and orthopedics. For instance, the embodiments disclosed herein can provide improved cutting of collagenous tissue to decrease transaction of collagen fibers, thus providing improved healing.

In many embodiments, where a tissue having folds is profiled with a measurement system, a layer of the tissue extending along the folds may define a tissue surface. An incision profile is generated based on the folds of the tissue surface to inhibit cutting of the tissue across the folds. This can either provide either a more uniform bed having fewer resected collagen fibers to receive a tissue graft, and/or provide a more uniform tissue graft having fewer resected collagen fibers to be placed on a recipient bed. In many embodiments, the tissue comprises corneal stromal tissue having lamella, and the lamella comprise collagen fibers extending along the lamella such that incising the tissue along the folds of the lamella inhibits resection of the collagen fibers.

In many embodiments, the apparatus comprises a cornea-profiling system for measuring a profile of a surface of a posterior or an anterior portion of the cornea, (e.g. a posterior or an anterior surface of the cornea), and a laser to generate a laser beam. A processor comprising a tangible medium is coupled to the laser and is configured to receive data from the cornea-profiling system. The tangible medium embodies instructions to determine a treatment profile based on the posterior or the anterior surface of the cornea. In many embodiments, the cornea-profiling system is configured to identify folds of the posterior surface of the cornea, and the processor comprises instructions to define the treatment profile with folds similar to the posterior surface of the cornea to inhibit resection of lamella of the corneal stroma. The profile of the cornea may comprise a representation of a three-dimensional elevation profile of the posterior surface of the cornea, and the laser beam pulse profile may extend at a depth within the stroma along a posterior portion of the cornea with folds similar to the surface folds of the posterior surface of the cornea so as to inhibit transecting the corneal lamella. A user interface can be coupled to the processor to allow the user to input a thickness of a corneal flap to be removed from the posterior surface, wherein the processor is configured to determine the treatment profile based on the thickness and a representation of a three-dimensional profile of the posterior surface of the cornea so as to inhibit transaction of the lamella of a corneal stroma. The user interface can be used to determine a maximum dimension (e.g. a diameter) across the treatment profile. In many embodiments, the user can input a parameter related to a thickness of tissue to be removed from the eye. The parameter may be an offset parameter of the treatment profile from the posterior surface profile of the cornea.

These improved techniques may generally be used for DMEK, DMAEK, as well as other known and newly-developed treatments of the eye that involve among other things, separating a thin layer from a cornea, or grafting a thin layer on a portion of the cornea, and/or transplanting a thin layer to a posterior portion of a cornea. Vision enhancements may be provided, for example, by inhibiting and/or reducing light scatter at the treated posterior surface of the treated cornea, and optionally by improvements in the overall smoothness and optical quality of the interior corneal surface by reducing localized irregularities such as wrinkles or folds. In some embodiments, the separation, grafting, and/or transplantation may be performed so as to inhibit or prevent overall changes in refractive shape (such as spherocylindrical corrections, or optionally, even gross high-order corrections such as spherical aberrations extending across the eye, etc.) of the posterior portion of the patient's cornea. On the other hand, in some other embodiments of the systems and methods described herein, overall changes in refractive shape may optionally be imposed in other portions of the cornea, in other optical structures of the eye, and/or in the posterior portion of the cornea.

In many embodiments, the apparatus can be used for methods for treating corneal disease, such as those diseases treated with Descemet's membrane automated keratoplasty procedures. The treatment profile can be determined based on the profile of the posterior surface of the cornea, and this treatment profile can be used to incise the posterior portion of the cornea. In addition, the treatment profile can be determined based on the profile of the anterior surface of the cornea, and this treatment profile can be used to incise the posterior portion of the cornea. An access incision profile can be generated with the processor system to incise an outer portion of the cornea near the limbus in order to access the anterior chamber and the posterior surface of the cornea. A flap of tissue can be removed from the posterior surface of the cornea, and a bed can be provided to receive graft tissue. A donor cornea can be treated with a treatment profile based on the posterior surface of the donor cornea so as to inhibit resection of folds of stromal lamella when the donor graft is prepared. The donor cornea may be incised with an access incision profile of the laser to provide an access incision in an outer portion of the cornea near the limbus. The tissue graft comprising a flap of donor tissue with endothelial cells can be removed from the donor cornea with decreased cutting of the lamella of the graft tissue.

In additional embodiments, the apparatus can be configured and used according to methods and apparatus for treating corneal disease such as those treated with the DMEK procedure, by aiding in the delivery of a needle or other elongate tubular structure to inflate the posterior flap away from the cornea. In this embodiment, to separate the Descemet's membrane from the stroma, the apparatus obtains a treatment profile based on the imaging profile of one or more of the posterior surface or the anterior surface, and makes an image-guided laser tunnel incision from the posterior surface to a location near the Descemet's membrane, such as a stromal location anterior to the Descemet's membrane. The tunnel incision can be used to guide the delivery of the needle which is used to introduce a fluid that separates the Descemet's membrane from the corneal lamella and that forms a pocket with the fluid, such as an air pocket. To separate the flap from the cornea, the apparatus can deliver a circular laser cut based on the image guidance. The laser can be used to cut the outer boundary of the flap so as to define a smooth perimeter of the flap. In many embodiments, the laser can be used to cut the anterior surface of the flap, which is subsequently separated from the stroma with the fluid introduced into the pocket. Alternatively, to define the anterior surface of the flap, the flap can be separated from the stroma along the lamella when the fluid is introduced without laser cutting.

This summary and the following detailed description are merely exemplary, illustrative, and explanatory and are not intended to limit, but to provide further explanation of the invention as claimed. Additional features and advantages of embodiments of this invention are set forth in the descriptions, drawings, and the claims, and in part will be apparent from the description, or may be learned by practice. The claims are incorporated herein by reference.

DETAILED DESCRIPTION

Figure 1:
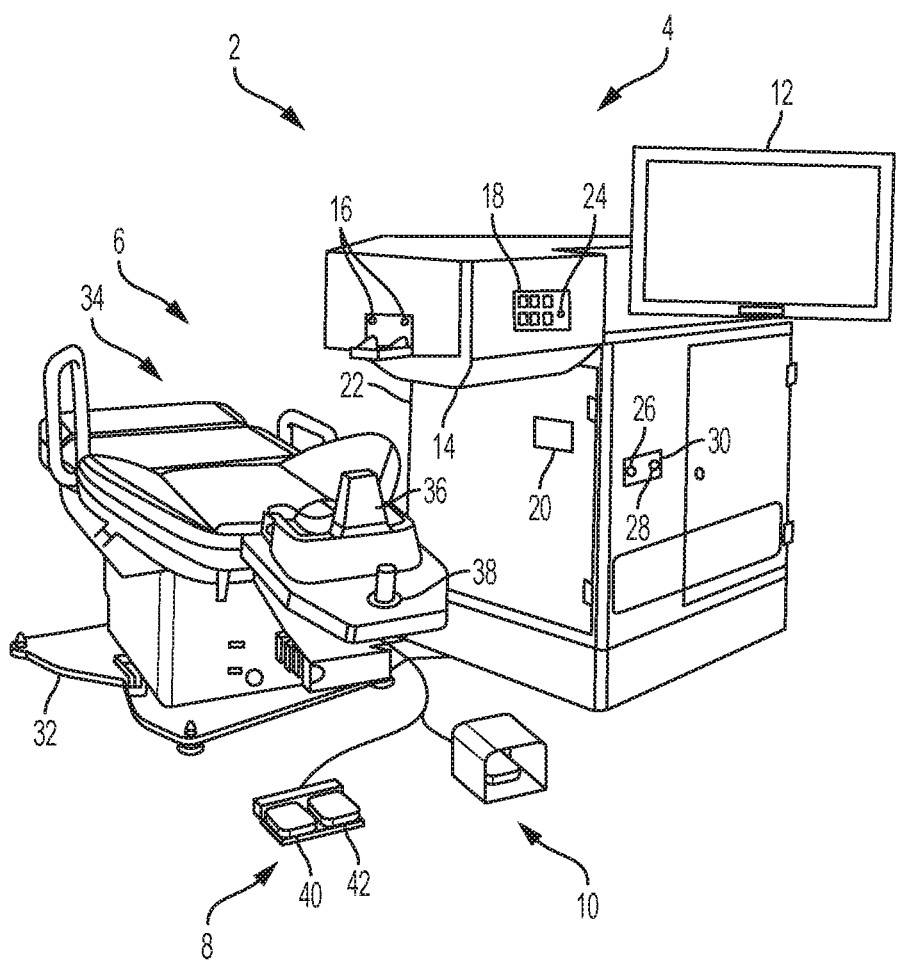
FIG. 1 shows a perspective view showing a laser eye surgery system according to many embodiments.

Methods and systems related to laser eye surgery are disclosed. In many embodiments, a pulsed laser is used to form precise incisions in the cornea, in the lens capsule, and/or in the crystalline lens nucleus. Although specific reference is made to tissue resection for laser eye surgery, the embodiments as described herein can be used in various ways with many surgical procedures and devices, including microkeratomes and procedures and devices used in orthopedic surgery, and robotic surgery.

The embodiments as describe herein are particularly well suit for treating tissue, such as with the surgical treatment of tissue with grafting. In many embodiments, the tissue comprises an optically transmissive tissue, such as tissue of an eye. The embodiments as described herein can be combined in various ways with a variety of known surgical procedures, including for example, cataract surgery, corneal incisions, keratoplasty, partial thickness keratoplasty, lamellar keratoplasty, deep lamellar keratoplasty, penetrating keratoplasty, DMEK, DMEAK, LASIK, and the treatment of astigmatism and corneal scarring. The embodiments as described herein are particularly well-suited for combination with procedures where it is desirable to form an accessible bed of stromal tissue where tissue can be treated either with photoablation or placement of a graft, such as for example, one or more of LASIK, partial thickness keratoplasty, lamellar keratoplasty, deep lamellar keratoplasty, and endothelial grafting procedures.

Methods and systems related to laser treatment of materials, and which can be used with eye surgery such as laser eye surgery are disclosed. A laser may be used to form precise incisions in the cornea, in the lens capsule, and/or in the crystalline lens nucleus, for example. The embodiments as described herein can be particularly well suited for increasing the accuracy of the cutting of the material such as tissue, for example.

In many embodiments, a patient interface coupled to the eye influences distortion of images and measurements of the eye obtained through the patient interface. In some embodiments, the patient interface may comprise a suction ring that can be placed on the eye near the limbus, wherein the placement of the suction ring on the eye can influence distortion of the cornea. In one or more embodiments, the patient interface may comprise an optically transmissive structure such as a flat plate or lens, and the optically transmissive structure can influence distortion of the second image. For example, the patient interface may add barrel distortion to images of the eye taken through the patient interface as compared with images of the eye taken when the patient interface has been removed from the eye and the eye has a natural configuration. Alternatively, the patient interface can be designed to add pincushion distortion, for example. The embodiments disclosed herein are particularly well-suited for combination with a patient interface having an optically transmissive element separated from the cornea. The curved lower surface of the optically transmissive lens structure separated from the cornea to urge gas bubbles away from the optical axis can increase the depth of field and range of the treatment, and the embodiments disclosed herein are ideally-suited for use with such a patient interface.

The embodiments disclosed herein are also suitable for combination with corneal measurement systems. The corneal measurement system may comprise a component of the laser surgery system, which allows the cornea to be measured with the corneal measurement system when the patient is lying on a patient bed coupled with the laser surgery system. Alternatively, the corneal measurement system may comprise a stand-alone corneal measurement system that is separate from the laser system, such as a measurement system located outside the operation room and in a different area of a physician's office.

The embodiments disclosed herein are well-suited for combination with laser surgery systems, such as the Catalys® Precision Laser System, commercially available from Optimedica. Such systems can be modified consistent with the teachings disclosed here and to more accurately measure and treat the eye.

As used herein, like characters such as reference numerals and letters described like elements.

As used herein, the terms anterior and posterior refers to known orientations with respect to the patient. Depending on the orientation of the patient for surgery, the terms anterior and posterior may be similar to the terms upper and lower, respectively, such as when the patient is lying in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

The processor system may comprise tangible medium embodying instructions of a computer program to perform one or more of the method steps as described herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatment reports stored on the data storage device can then be accessed at a later time for any suitable purpose such as, for example, printing from an external computer in the case where the user is without access to network-based printing.

Figure 2:
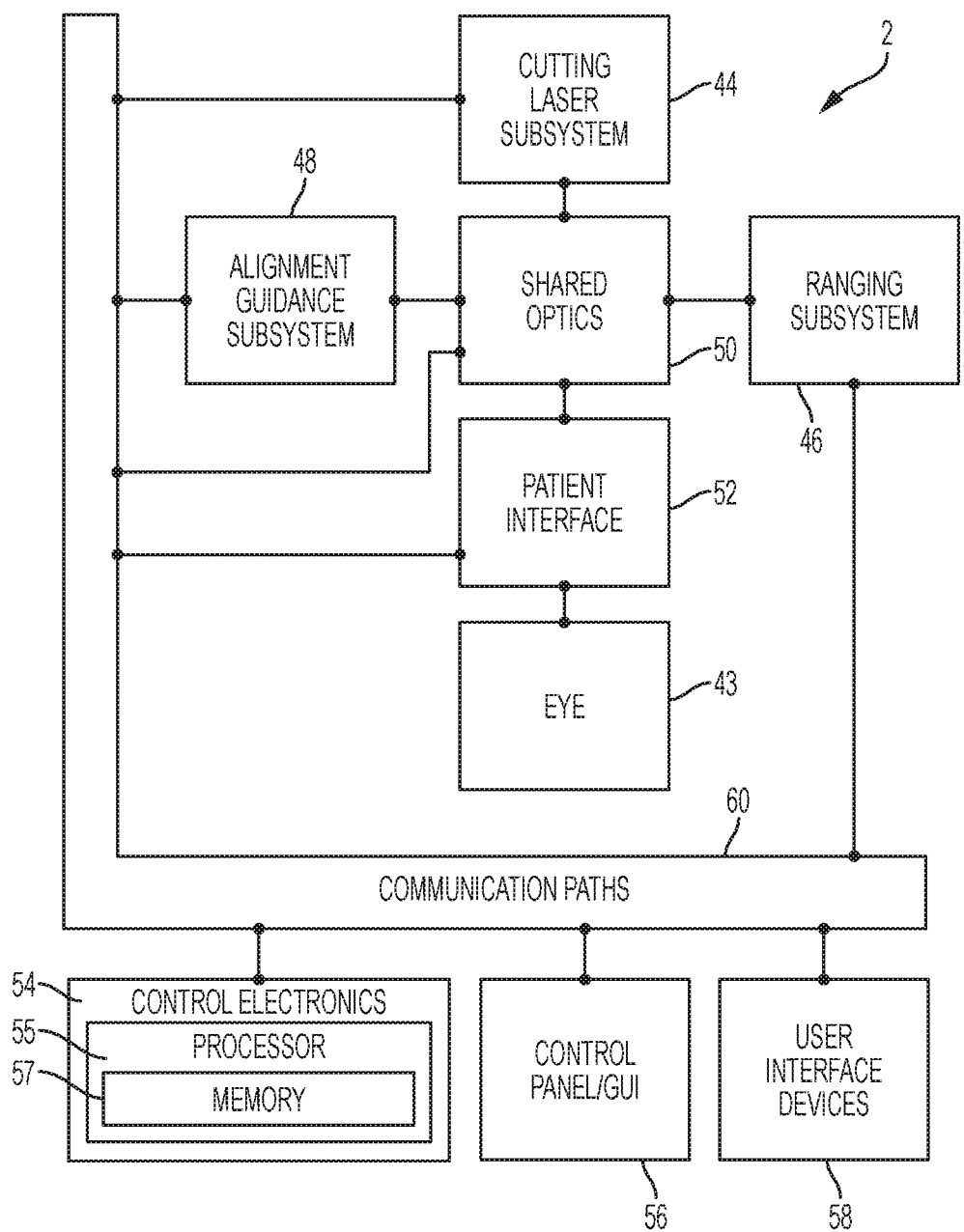
FIG. 2 shows a simplified block diagram showing a top level view of the configuration of a laser eye surgery system according to many embodiments.

FIG. 2 shows a simplified block diagram of the system 2 coupled with a patient eye 43. The patient eye 43 comprises a cornea 43C, a lens 43L and an iris 431. The iris 431 defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates ultra-short pulsed laser technology, specifically, femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
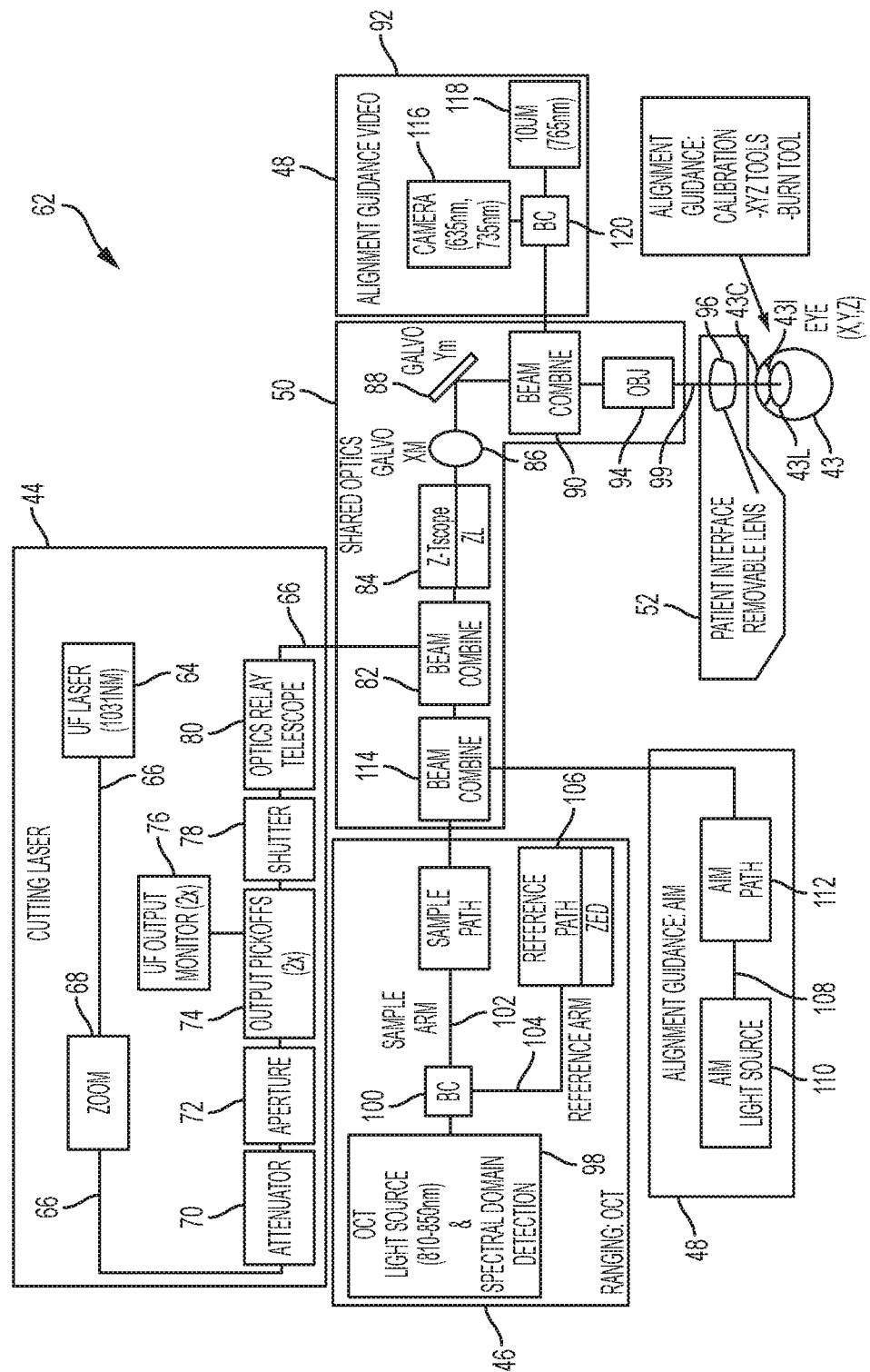
FIG. 3A shows a simplified block diagram illustrating the configuration of an optical assembly of a laser eye surgery system according to many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically, to achieve optimal performance the transmission through this aperture is set between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3 includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., as described in U.S. Pat. Nos. 5,748,898; 5,748,352; 5,459,570; 6,111,645; and 6,053,613, which are incorporated by reference herein.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
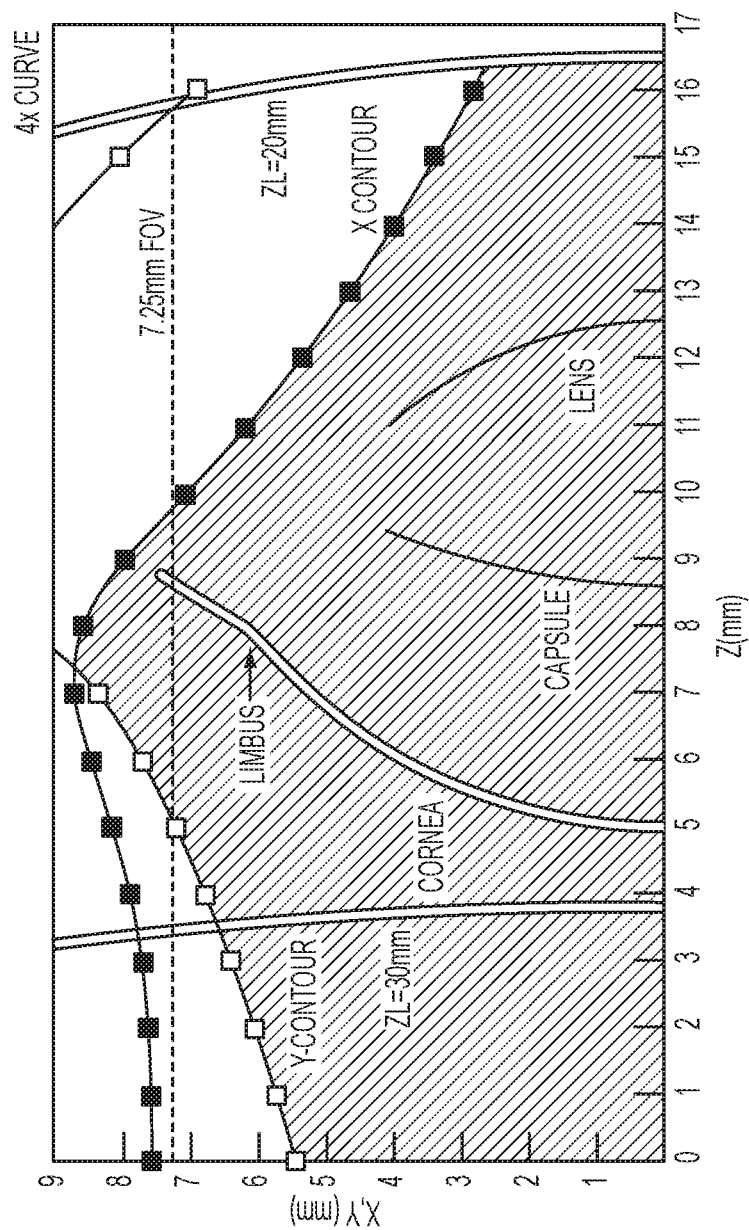
FIG. 3B shows a mapped treatment region of the eye comprising the cornea, the posterior capsule, and the limbus according to many embodiments.

FIG. 3B shows a mapped treatment region of the eye comprising the cornea, the posterior capsule, and the limbus. The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the center of the cornea to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 4A:
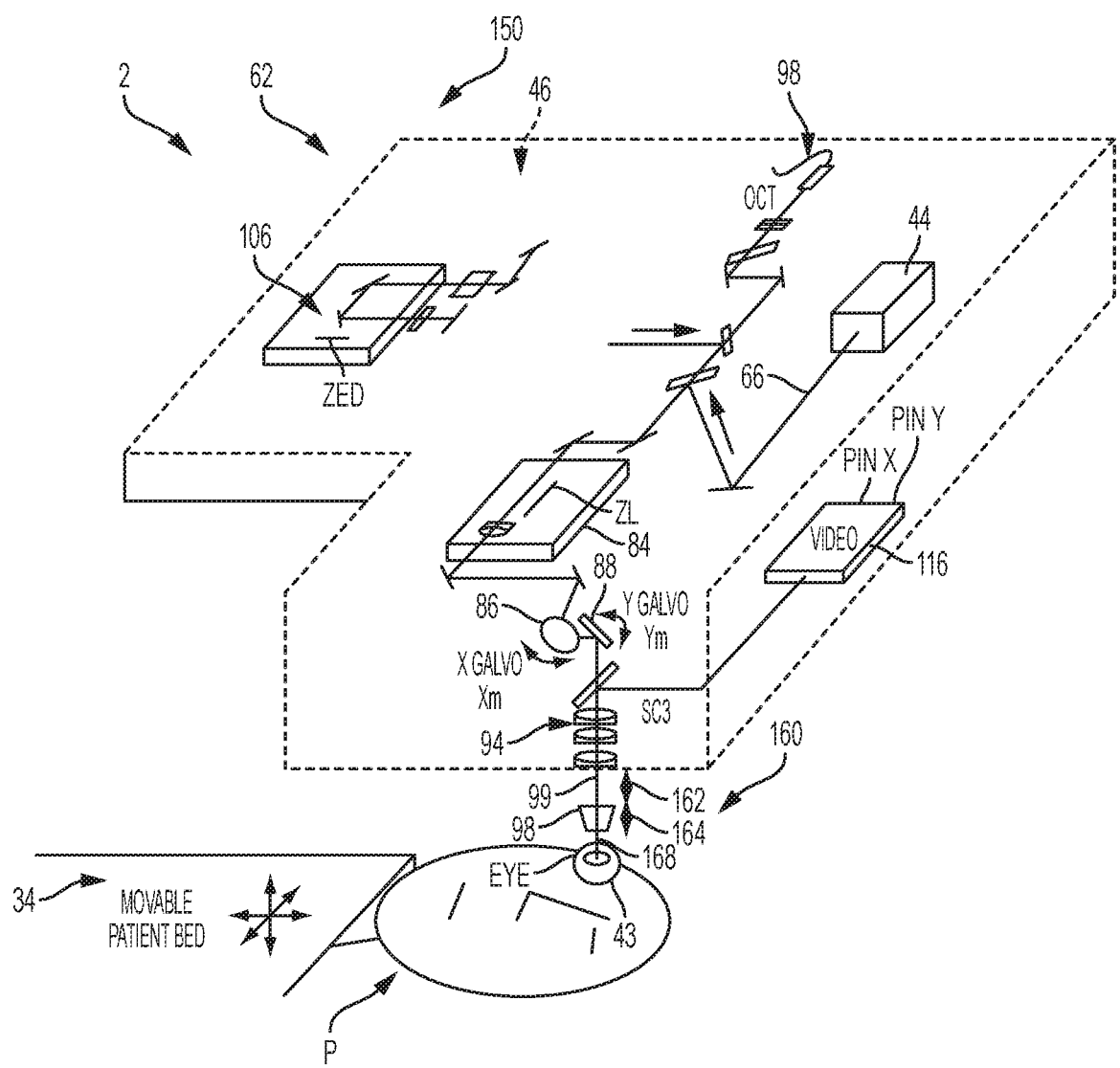
FIG. 4A shows correspondence among movable and sensor components of the laser delivery system according to many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
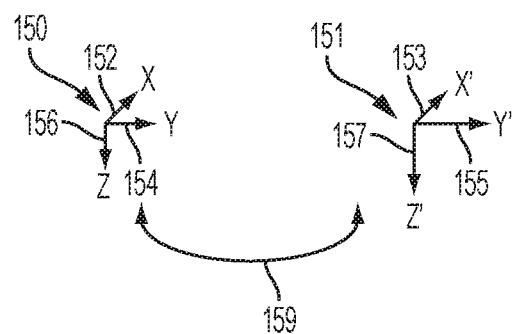
FIG. 4B shows mapping of coordinate references from an eye space coordinate reference system to a machine coordinate reference system according to many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferable the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 5A:
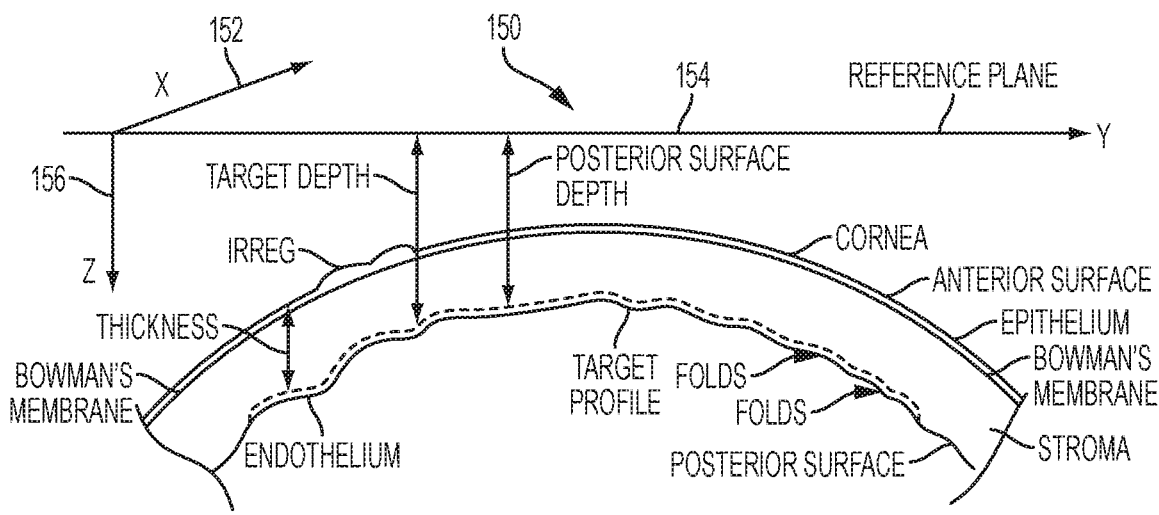
FIG. 5A shows a cornea of an eye having endothelial folds and a treatment profile according to embodiments.

FIG. 5A shows a cornea of an eye having stromal and endothelial folds and a treatment profile. The eye comprises a cornea. The cornea has an anterior side portion and a posterior side portion. The cornea comprises an epithelial layer, a Bowman's membrane, a stroma and an endothelium. A Bowman's membrane is located on the anterior side of the eye between the epithelium and the stroma. Above Bowman's membrane lies the epithelium. The epithelium when covered with a tear film corresponds to an anterior surface of the cornea and comprises refractive power of the eye. The stroma comprises a majority of the thickness of the cornea and the stroma extends from Bowman's membrane to Descemet's membrane. Descemet's membrane is located between the endothelium and the stroma.

The eye is shown in relation to eye coordinate reference frame 150 having x, y and z axes as described herein. The eye may comprise an irregular posterior surface comprising the endothelium. The endothelium, stroma and Descemet's membrane may comprise folds and the folds may be visible through slit lamps in accordance with some embodiments.

In many embodiments, the eye comprises a degraded optical tissue surface. The degraded optical tissue surface may comprise folds of the posterior stromal portion or irregularities of the epithelium and combinations thereof. For example, the anterior surface of the cornea may comprise an irregularity such as an irregular epithelium and epithelial irregularities. The epithelial irregularities may comprise one or more irregularities that affect light transmission and may scatter light. On the posterior side of the cornea the stroma may comprise folds and the folds can affect light refraction and transmission and in some embodiments can provide light scatter so as to degrade vision.

Work in relation to embodiments suggests that the irregular posterior surface of the cornea can be related to folds in the stroma and that by providing a target profile corresponding to the irregular folds, the endothelium and Descemet's membrane can be removed more uniformly. In many embodiments a portion of the stroma is removed in a manner that decreases transection of the collagen fibers of the stroma. The lamellae of the cornea comprise collagen fibers that extend along the stroma. The incision profile can extend along the lamella to inhibit resection of the collagen fibers.

In many embodiments, a tissue surface can be defined based on one or more of the stromal lamella, the endothelium, or Descemet's membrane, for example. The tissue surface may extend along the lamella, for example between the lamella, and the incising treatment profile can be configured so as to extend along the tissue surface. As light scattering of the lamella can vary with the angle of the lamella and collagen fibers, the folds of the lamella and the tissue surface of the lamella can be profiled with the measurement system having sufficient resolution capable of detecting the stromal folds as described herein.

The eye can be profiled in one or more of many ways as described herein. With reference to coordinate frame 150, the coordinate frame can be used to determine the target depth of the treatment profile. The treatment profile can be determined with respect to a reference frame such as a reference plane as described herein and the reference plane can be referenced with respect to an optical surface of the laser delivery system such as the posterior-most portion of the patient interface transmission structure such as the lens as described herein. The eye can be profiled so as to determine a posterior surface depth with respect to the reference plane. The posterior surface depth can be measured along the x and y axes so as to describe a three-dimensional depth profile. The three-dimensional posterior surface depth profile can be used to determine the target depth profile of the cornea. The target depth profile can be programmed with the patient. The target depth may also be programmed by the user with a user-specified input, such as for example, a particular distance from the posterior surface. For example, a user may specify a depth a distance between the posterior surface and the target profile of 10 microns and the software can be programmed to determine the target depth corresponding to the target profile. In many embodiments, the cornea comprises a thickness and the thickness varies along the cornea and the cup profile is configured so as to vary in relationship to the thickness to provide a more uniform treatment. The target depth can be programmed into the laser system as described herein.

Figure 5B:
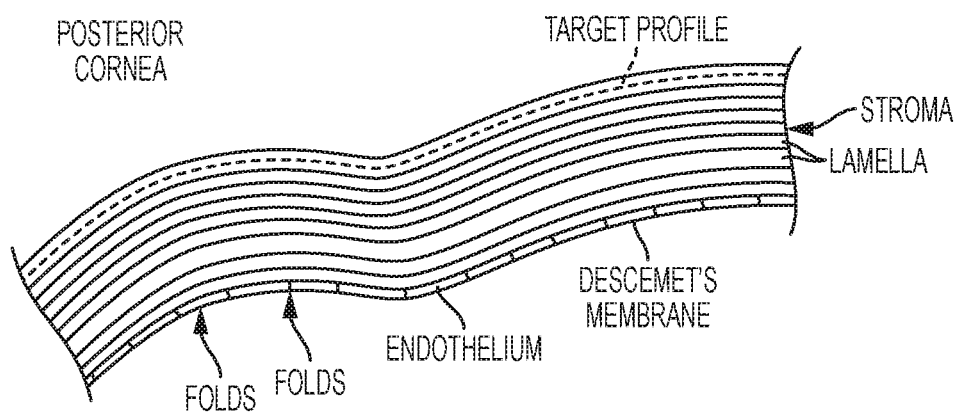
FIG. 5B shows a magnified view of an eye as in FIG. 5A, including folds in stromal lamella and a target profile to decrease incisions across the lamella according to embodiments.

FIG. 5B shows a magnified view of an eye as in FIG. 5A, including folds in stromal lamella and a target profile to decrease incisions across the lamella, of the posterior portion of the cornea as described herein. The posterior portion of the cornea comprises the endothelium, Descemet's membrane and stromal lamella as described herein. As shown with reference to FIG. 5B, the folds may comprise folds of the endothelium and Descemet's membrane and the stromal lamella. The lamella and the stroma may comprise folds similar to the folds of Descemet's membrane and the endothelium so that by programming the treatment to have a target depth reference to the frame, similar to the profile of the posterior surface of the cornea, the cutting of stromal lamella can be decreased substantially. For example, as shown in FIG. 5B, the target profile varies so as to decrease and inhibit cutting through the stromal lamella and so provides a more uniform removal of tissue in accordance with embodiments.

Figure 5C:
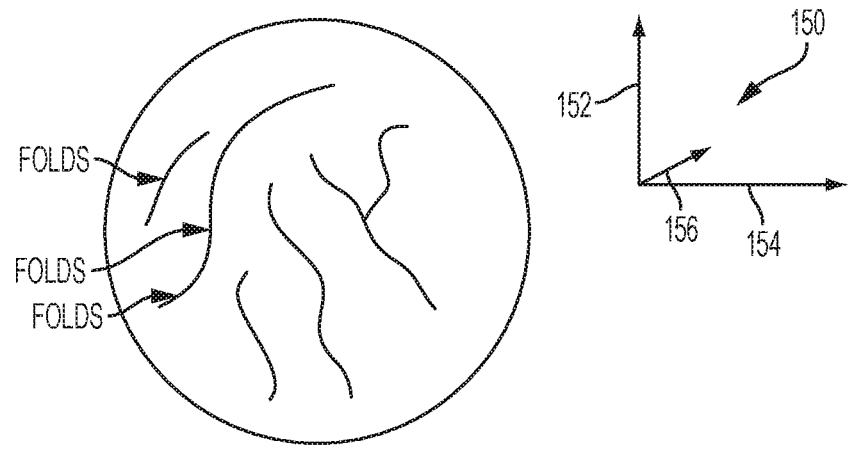
FIG. 5C shows a front view of an eye as in FIG. 5A, including folds in Descemet's membrane and the lamella according to embodiments.

FIG. 5C shows a front view of an eye as in FIG. 5A, including folds in Descemet's membrane and the lamella. The view shows the thickness of the cornea in accordance with embodiments. FIG. 5C shows an example of a three dimensional representation of the thickness of the cornea that can be used to determine the treatment profile. The incising treatment profile comprises a maximum dimension across, such as a diameter of a circle as shown in FIG. 5C. Although the treatment profile is show to extend in a circular pattern, the treatment profile may comprise one or more of many shapes such as oval, rectangular, square, regular or irregular. Also, the outer boundary of the profile where lamellae are resected may comprise an interlocking profile such as a jig-saw pattern, for example. The folds as shown in FIG. 5C correspond to the varying thickness of the three dimensional depth profile of the thickness of the cornea. The three dimensional thickness profile can be used to determine the target profile as described herein. For example, the target profile may comprise a three dimensional target profile or a representation of the three dimensional profile corresponding to a three dimensional representation of the thickness of the cornea so as to provide a cut into the stromal tissue that decreases cutting across the stromal lamella. The coordinate reference frame 150 is shown with reference to FIG. 5C and can be used to determine the thickness profile of the cornea and the appropriate depth of the incision. As described with reference to FIG. 5A, the target profile can be based on the posterior surface of the cornea and the thickness, for example, 5 microns, 10 microns or 15 microns, can be programmed by a user so as to provide removal of the posterior portion of the cornea so as to prepare the bed for placement of the graft tissue via donor.

Figure 5D:
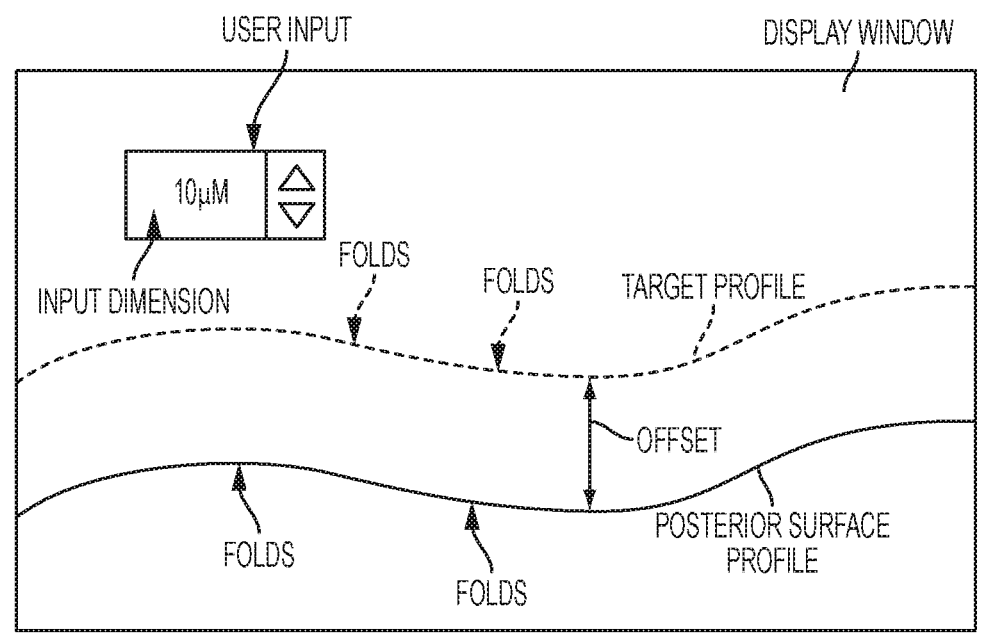
FIG. 5D illustrates a display window of the laser system showing folds of the posterior cornea and a target laser pulse profile having folds to accommodate folds of the posterior surface according to embodiments.

FIG. 5D illustrates a display window of the laser system showing folds of the posterior cornea and a target laser pulse profile having folds to accommodate folds of the posterior surface. The display window can be combined with one or more other windows of the display, and can be combined with components of the user interface as described herein. The display comprises a user input to set an aspect of the target incision profile, such as a dimension of the profile in relation to the posterior surface of the cornea. The user can input a parameter that is used to define the target profile of the laser beam incision based on the posterior surface profile, for example with an offset to the posterior surface profile.

In many embodiments, the target incision profile of the laser beam is dimensioned in relation to the measured posterior surface of the cornea such that folds of the target profile correspond to folds of the posterior surface. For example, the posterior surface profile can be one or more of offset or scaled to provide the target profile such that the target profile comprises the folds of the posterior surface that correspond to folds of the underlying stroma in at least some embodiments. In many embodiments, the offset of the posterior surface profile corresponds to a thickness of the flap removed from the posterior portion of the cornea. The posterior surface profile may comprise a representation of a three dimensional surface profile of the posterior surface of the cornea, for example.

In many embodiments, the folds of the stroma can be measured directly with a high resolution tomography system configured to provide sufficiently high resolution in three dimensions and software configured to identify the folds of stromal tissue from the images of the stromal tissue. For example, the tomography system may comprise an optical coherence tomography system, or a confocal tomography system, or combinations thereof, configured to provide high resolution three dimensional tomography of the cornea. Along a continuous depth image, the folds may be observed as variations of intensity of the image.

Figure 6:
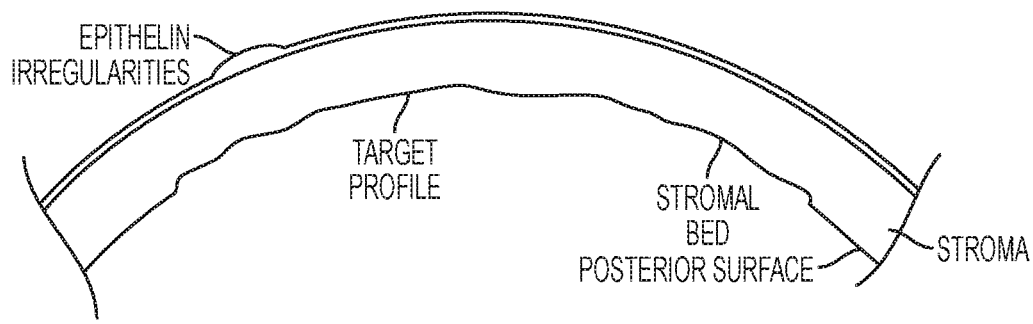
FIG. 6 shows a cornea as in FIG. 5A with Descemet's membrane, the endothelium, and a portion of the stroma removed along the treatment profile according to embodiments.

FIG. 6 shows a cornea as in FIG. 5A with Descemet's membrane, the endothelium, and a portion of the stroma removed along the treatment profile. The diseased endothelium and Descemet's membrane can be removed once the target probe the profile has been used to treat the cornea with the plurality of pulses as described herein such that the diseased tissues can be resected. As shown in FIG. 6 the stromal bed is exposed on the posterior side of the cornea. The stromal bed can be accessed through an incision in the cornea, for example, as can be performed with the NEK. In many embodiments, the stromal incision is performed with the laser system in the manner similar to as may be done with cataract surgery, the laser system can be used to cut the cornea at the periphery of the cornea to provide access to the stromal bed. The target profile is shown to provide the shape of the stromal bed with reference to FIG. 6.

Figure 7A:
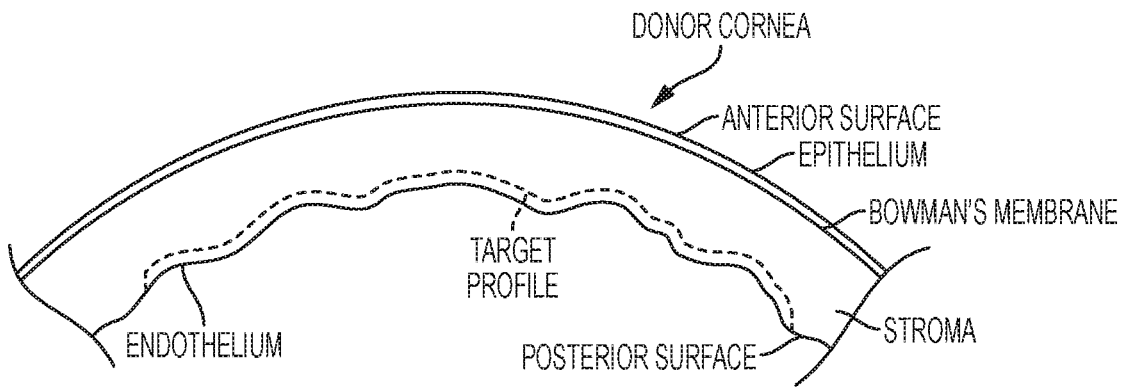
FIG. 7A shows a donor cornea and a donor treatment profile to remove a graft for explantation according to embodiments.

FIG. 7A shows a donor cornea and a donor treatment profile to remove a graft for explantation. The donor cornea comprises structures similar to the cornea being treated of the recipient. The donor cornea comprises an anterior surface and a posterior surface. An epithelium generally defines the anterior surface of the cornea. A Bowman's membrane is located between the stroma and epithelium of the donor cornea. A target profile is shown in the donor cornea and the target profile can be defined similarly to the target profile of the treated eye receiving the donor graft. For example, the target profile thickness of the donor cornea may describe a thickness similar to the thickness of the eye being treated and the target profile can be defined with respect to the posterior surface of the donor cornea so as to provide a three dimensional target profile defined based on a three dimensional representation of the posterior surface; for example so as to provide a thickness of about 10 microns. In many embodiments the donor cornea may comprise a slightly swollen cornea such that the target profile may correspond to irregularities of the posterior surface of the cornea so as to inhibit cutting and transection of the lamella of the donor cornea stroma.

Figure 7B:
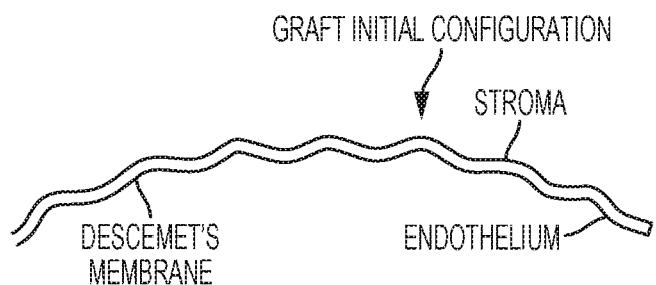
FIG. 7B shows an initial profile of the graft donor tissue prior to removal from the eye as in FIG. 7A.

FIG. 7B shows an initial profile of the graft donor tissue prior to removal from the eye as in FIG. 7A. The graft tissue comprises Descemet's membrane and an endothelium and a portion of the stroma, each from the donor cornea. As shown in FIG. 5B, the graft comprises an initial configuration corresponding to the configuration of the graft within the cornea of the eye. The graft shown in FIG. 7B may comprise a slightly compressed configuration within the donor cornea due to swelling of the corneal tissue. It may be related to the state of the donor cornea when the graft is harvested.

Figure 7C:
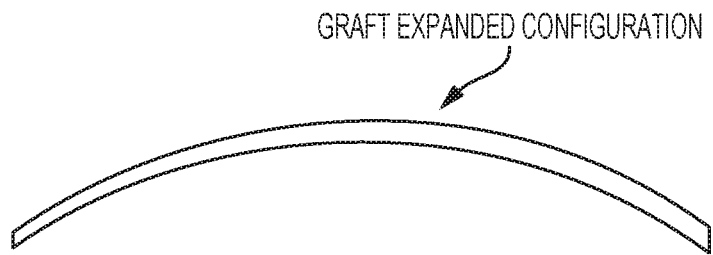
FIG. 7C shows the graft tissue as in FIGS. 7A and 7B in an expanded configuration subsequent to removal from the eye.

FIG. 7C shows the graft tissue as in FIGS. 7A and 7B in an expanded configuration subsequent to removal from the eye. The graft may comprise a smooth surface or a smoother surface than is shown in FIG. 7B when the tissue has been resected from the donor cornea. The smoother surface can be provided as the transection of the stromal lamella had been decreased.

Figure 8:
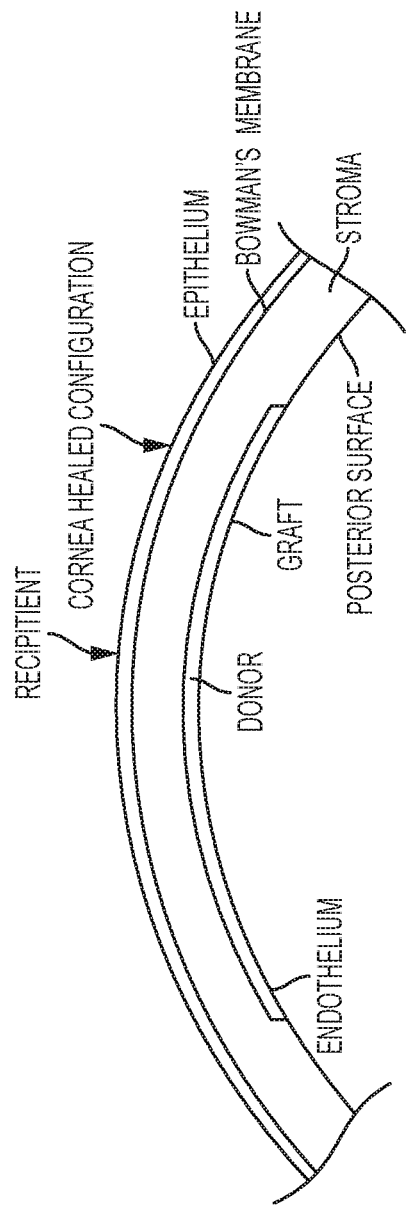
FIG. 8 shows the graft as in FIGS. 7A to 7C placed in the recipient cornea subsequent to healing of the eye according to embodiments.

FIG. 8 shows the graft as in FIGS. 7A to 7C placed in the recipient cornea subsequent to healing of the eye. The recipient cornea is shown in a healed configuration subsequent to placement of the graft tissue comprising Descemet's membrane, the donor Descemet's membrane, the donor endothelium and the donor stroma. As the endothelium in the healed eye can be healthy, the thickness and pumping of the corneal stroma has been restored, such that the stroma comprises a smoother surface anteriorly and posteriorly due to the improved health of the endothelium. The graft may comprise a smooth surface and is capable of smoothing so as to correspond to the shape of the bed of the cornea having the decreased thickness.

The structures of the recipient cornea as shown in FIG. 8 are similar to the structures of the recipient cornea shown above and comprise an epithelium, Bowman's membrane stroma, endothelium and Descemet's membrane, for example, and the graft, and the profile of the graft, are shown with reference to the healed cornea and the donor graft is shown on the posterior surface of the cornea.

FIGS. 9A to 9D show forming a pocket with a fluid in order to separate a posterior corneal flap from the cornea along lamella of the cornea. The fluid can be used to form the pocket in combination with embodiments as described herein.

Figure 9A:
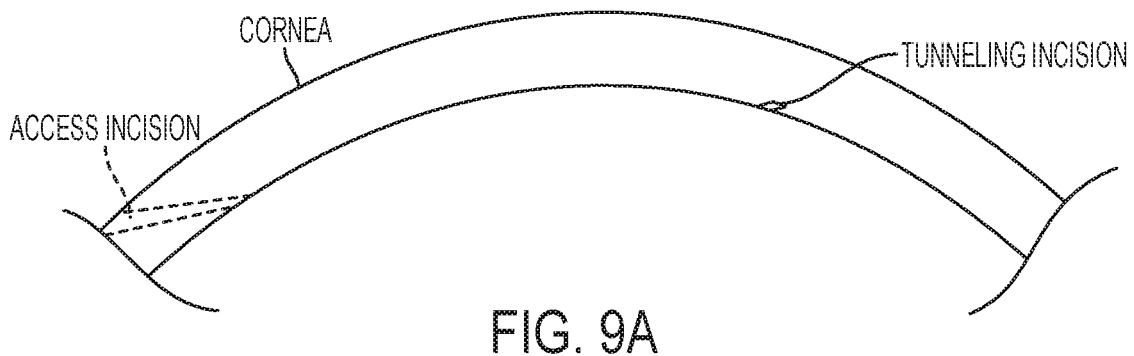
FIGS. 9A to 9D show forming a pocket to separate a posterior corneal flap from the cornea along lamella of the cornea according to embodiments.

FIG. 9A shows an access incision can be formed in the cornea to provide access to the anterior chamber of the eye. A tunneling incision can be formed in a posterior surface of the cornea to allow a needle to penetrate the posterior cornea to a predetermined depth based on the depth of the tunneling incision. The tunneling incision and the access incision can be formed with image guided laser beam pulses as described herein. The tunneling incision can be formed in response to one or more of the posterior surface profile and the anterior surface profile so that the tunneling incision extends a predetermined depth from the posterior surface of the cornea to a target depth at which the cornea lamella are to be separated in order to provide the flap of removed tissue.

Figure 9B:
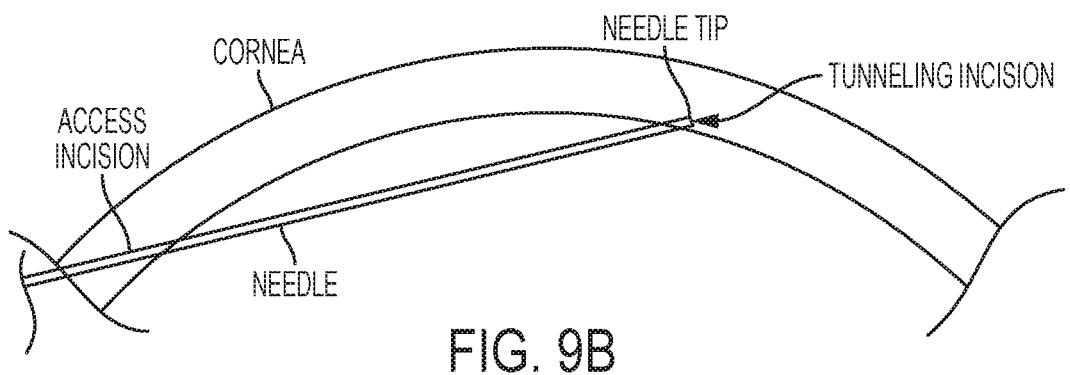

FIG. 9B shows a needle inserted through the access incision and into the tunneling incision. The tunneling incision can be sized to fit the needle in order to inhibit passage of air between the incision and the needle. Although a needle is shown, the structure introduced into the eye to provide the fluid that forms the pocket may comprise one or more of many elongate structures having an inner channel to provide fluid such as a tube, a hypo tube, a cannula or a micro-catheter, for example.

While the tunneling incision can be shaped and oriented in one or more of many ways, in many embodiments the tunneling incision comprises an elongate axis oriented toward the access incision of the cornea, which allows the needle to be advanced along the tunneling incision when the needle extends through the access incision. In many embodiments the elongate axis of the tunneling incision is aligned with an elongate axis of the needle when the needle has been advanced to the end of the tunneling incision.

Figure 9C:
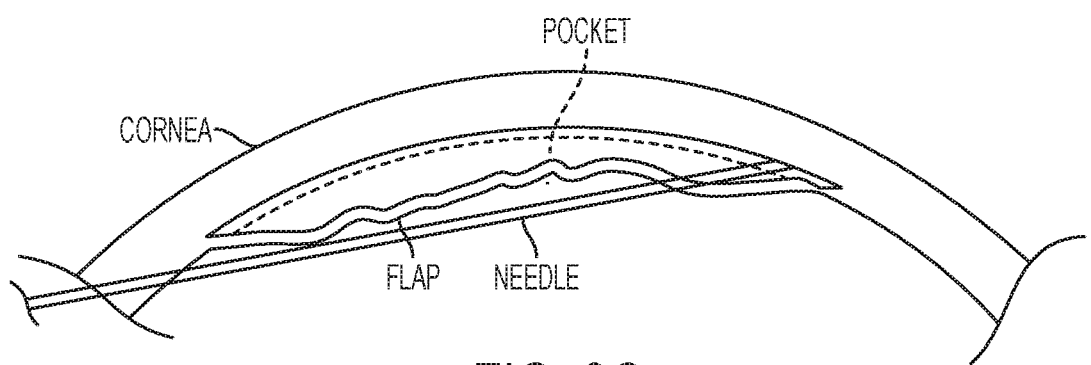

FIG. 9C shows a pocket formed with introduction of a fluid into the cornea through the tip of the needle positioned along the tunneling incision. The introduction of fluid separates the cornea along the lamella in order to separate a flap comprising Descemet's membrane from the cornea. A sufficient amount of fluid can be introduced in order to separate the flap from the cornea and provide a volume to the pocket such that the flap is separated from the cornea. The fluid introduced into the pocket may comprise one or more of many fluids such as a liquid, a gel, a viscoelastic, a gas, or air, for example.

Figure 9D:
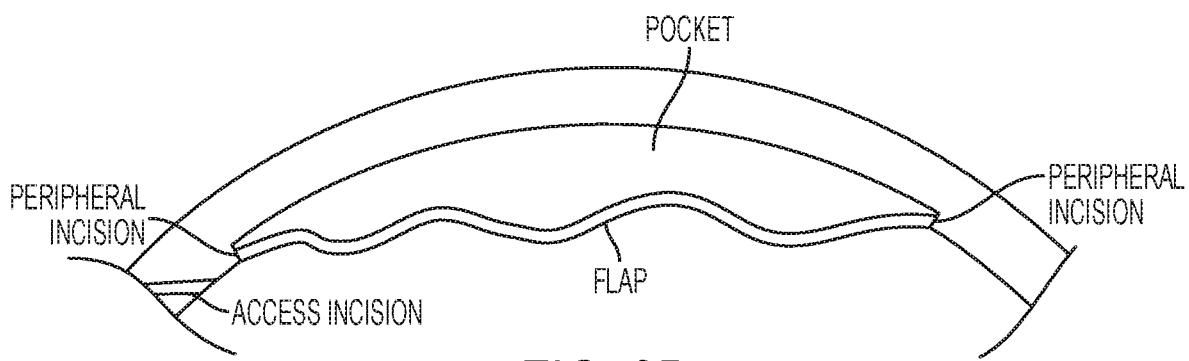

FIG. 9D shows one or more peripheral incisions near an outer boundary of the flap to provide a smooth outer boundary of the flap. The peripheral incisions can be made before the flap is separated from the cornea or after the flap is separated from the cornea, for example. The peripheral incision may comprise a circular incision that defines an outer circumference of the flap. The peripheral incision may comprise one or more of many shapes such as non-circular shapes, for example.

Figure 10:
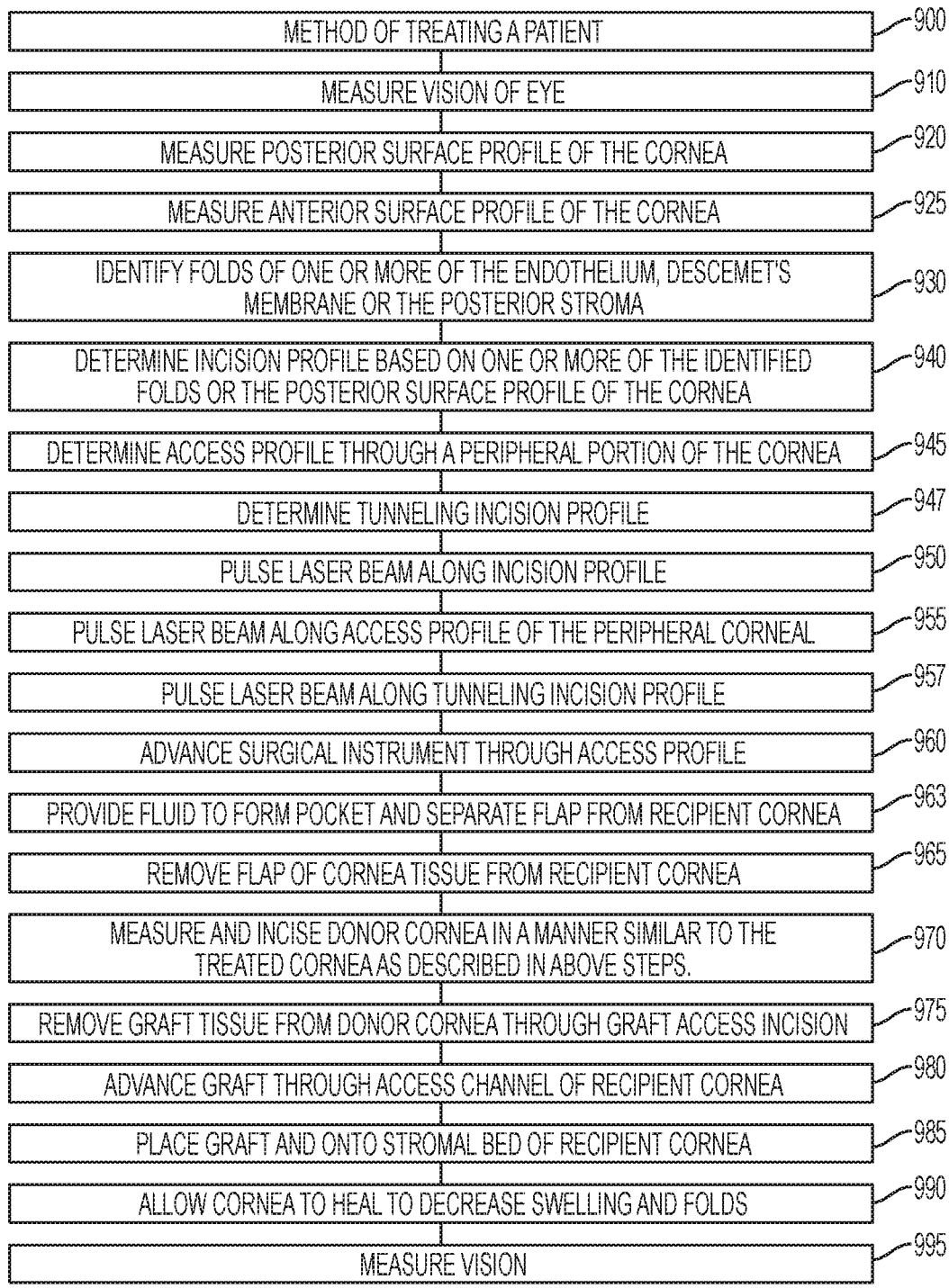
FIG. 10 shows a method of treating a patient according to embodiments.

FIG. 10 shows a method 900 of treating a patient, in accordance with embodiments.

At a step 910, vision of the eye is measured.

At a step 920, the posterior surface profile of the cornea is measured.

At a step 925, the anterior surface profile of the cornea is measure.

At a step 930, folds are identified of the posterior surface of the cornea. The posterior surface may comprise folds of the endothelium, Descemet's membrane, or stroma, as described herein, for example. Alternatively or in combination, the folds can be folds of the posterior stroma, such as posterior stromal folds.

At a step 940, an incision profile is determined based on one or more of the identified folds or the posterior surface profile of the cornea.

At a step 945, an access profile is determined through which a peripheral portion of the cornea is accessed.

At a step 947, a tunneling incision profile is determined as described herein.

At a step 950, the laser beam is pulsed along the incision profile.

At a step 955, the laser beam is pulsed along the access profile to provide access to the anterior chamber of the eye.

At a step, 957, the laser beam is pulsed along the tunneling incision profile to form the tunneling incision.

At a step 960, a surgical instrument is advanced through the access profile. At a step 965, the donor cornea is measured and incised in a manner similar to the treated cornea, as described above.

At a step 963, fluid is provided to form a pocket and separate the flap from the recipient cornea.

At a step 965, a flap of cornea tissue comprising the endothelium, Descemet's membrane and posterior stroma is removed from the recipient cornea.

At a step 970, the donor cornea is measured and incised in a manner similar to the treated cornea as described herein.

At a step 975, graft tissue is removed from the donor cornea through a graft incision.

At a step 980, the graft is advanced to the access channel of the recipient cornea and the graft can be folded, shaped or rolled in one or more of many ways to provide a decreased incision to the recipient cornea.

At a step 985, the graft is placed onto a stromal bed of the recipient cornea.

At a step 990, the cornea is allowed to heal to decrease swelling and folds.

At a step 995, vision of the patient is measured and improves.

FIG. 10 shows a method of treating an eye in accordance with some embodiments, and a person of ordinary skill in the art will recognize many adaptations and variations based on the teachings provided herein. For example, the steps can be performed in a different order, and the steps can be removed or repeated. Also, the steps may comprise substeps.

The tangible medium of the processor as described herein can embody instructions to perform one or more steps of the method, for example instructions of a computer program to perform one or more steps of the method.

While preferred embodiments of this disclosure have been shown and described in an exemplary form with a certain degree of particularity, those skilled in the art will understand that the embodiments are provided by way of example only, and that various modifications, alternative constructions, changes, substitutions, and variations can be made in the embodiments without departing from the spirit or scope of the invention. Thus, it is intended that this invention cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method of treating a cornea of an eye, the method comprising:
measuring a profile of a posterior portion of the cornea;
identifying one or more folds in the profile of the posterior portion of the cornea; and
incising the cornea using a laser beam according to an incision profile which is based on the profile of the posterior portion of the cornea and has folds corresponding to the folds in the profile of the posterior portion of the cornea, wherein the incision profile removes a uniform thickness of the cornea and inhibits resection of lamella of the stroma of the cornea.

2. The method of claim 1, wherein the cornea is treated so as to inhibit light scatter at a treated posterior surface of the treated cornea.

3. The method of claim 1, wherein the incision profile extends along the posterior portion in response to the folds to inhibit transecting the lamella of the stroma.

4. The method of claim 1, wherein the posterior portion comprises an irregular posterior surface, and wherein the incision profile provides an irregular incision profile corresponding to the irregular posterior surface.

5. A method as in claim 4, wherein the irregular posterior surface corresponds to folds of stromal lamella of the cornea and wherein the irregular incision profile decreases transaction of the stromal lamella.

6. The method of claim 5, further comprising obtaining a donor graft from a donor cornea, including:
measuring a profile of a posterior portion of the donor cornea, wherein the donor cornea comprises an irregular donor cornea posterior surface corresponding to donor folds of donor stromal lamella of the donor cornea; and
incising the donor cornea using a laser beam according to an irregular donor incision profile which has folds corresponding to the donor folds of the donor stromal lamella, wherein the incision removes a uniform thickness of the donor cornea and decreases transaction of the donor stromal lamella.

7. The method of claim 6, further comprising:
incising a limbal portion of the cornea using a laser beam to provide an access incision of the limbal portion of the cornea in order to access to the posterior portion of the cornea;
removing a flap of the treated cornea through the access incision; and
inserting the donor graft through the access incision.

8. The method of claim 1, wherein the folds in the profile of the posterior portion of the cornea corresponds to folds of a Descemet's membrane of the cornea and wherein the incision profile has folds corresponding to the folds of the Descemet's membrane.

9. The method of claim 8, further comprising obtaining a donor graft from a donor cornea, including:
measuring a profile of a posterior surface of the donor cornea, wherein the donor cornea has donor folds in at least a donor Descemet's membrane of the donor cornea and wherein the donor folds are mapped with a donor posterior surface profile; and
incising the donor cornea using a laser beam according to a donor incision profile which has folds corresponding to the donor folds of the donor Descemet's membrane.

10. The method of claim 9, further comprising:
incising a limbal portion of the cornea using a laser beam to provide an access incision of the limbal portion of the cornea in order to access to the posterior portion of the cornea;

removing a flap of the treated cornea through the access incision; and inserting the donor graft through the access incision.

11. The method of claim 1, further comprising:

incising a limbal portion of the cornea using a laser beam to provide an access incision of the limbal portion of the cornea in order to access to the posterior portion of the cornea;

removing a flap of the treated cornea through the access incision; and inserting a flap of donor tissue through the access incision.

* * * * *